(12) United States Patent
Resnic (10) Patent No.: US 9,351,866 B1
(45) Date of Patent: May 31, 2016

(54) FLUTED CONDOM

(71) Applicant: Daniel Resnic, Marina Del Rey, CA (US)

(72) Inventor: Daniel Resnic, Marina Del Rey, CA (US)

( * ) Notice: Subject to any disclaimer, the term of this patent is extended or adjusted under 35 U.S.C. 154(b) by 0 days.

(21) Appl. No.: 14/664,605

(22) Filed: Mar. 20, 2015

(51) Int. Cl.
*A61F 6/04* (2006.01)

(52) U.S. Cl.
CPC ........................................ *A61F 6/04* (2013.01)

(58) Field of Classification Search
CPC ........................................................ A61F 6/04
See application file for complete search history.

(56) References Cited

U.S. PATENT DOCUMENTS

| 4,798,600 | A | * | 1/1989 | Meadows | A61F 6/04 128/839 |
| 4,919,149 | A | * | 4/1990 | Stang | A61F 6/04 128/842 |
| 5,076,287 | A | * | 12/1991 | Johnson | A61F 6/04 128/842 |
| 5,158,556 | A | * | 10/1992 | Starley | A61F 6/04 128/842 |
| 5,370,131 | A | * | 12/1994 | Hess | A61F 6/04 128/842 |
| 5,885,205 | A | * | 3/1999 | Kassman | A61F 5/41 128/842 |
| 5,954,054 | A | * | 9/1999 | Johnson | A61F 6/04 128/844 |
| 6,223,747 | B1 | | 5/2001 | Rudge et al. | |
| 6,983,751 | B2 | * | 1/2006 | Osterberg | A61F 6/04 128/842 |
| 7,047,975 | B2 | | 5/2006 | Austin et al. | |
| 7,434,581 | B1 | | 10/2008 | Reddy et al. | |
| 8,136,528 | B2 | | 3/2012 | Resnic | |
| 8,443,809 | B2 | | 5/2013 | Hui | |
| 8,667,968 | B2 | | 3/2014 | Resnic | |
| 2009/0205668 | A1 | * | 8/2009 | Morissette | A61F 6/04 128/844 |

* cited by examiner

*Primary Examiner* — Alireza Nia
*Assistant Examiner* — Tarla Patel
(74) *Attorney, Agent, or Firm* — Trojan Law Offices (57) ABSTRACT

This invention relates to condoms, prophylactics and contraceptive devices having a thick shape-retaining sheath body with an open end and a closed end, and a plurality of longitudinal flutes on the sheath body.

8 Claims, 6 Drawing Sheets

FLUTED CONDOM

FIELD OF THE INVENTION

This invention relates to a condom for contraceptive and prophylactic use. In particular, this invention relates to an improved condom having a fluted, non-rolled design.

BACKGROUND OF THE INVENTION

The present invention is directed to overcoming problems associated with traditional thin membrane rolled condoms in the fight against sexually transmitted diseases, including the spread of the human immunodeficiency virus (HIV) that can result in acquired immune deficiency syndrome (AIDS), while improving sexual sensation for the user.

Protection from sexually transmitted diseases is a public health concern that affects all people, regardless of sexual orientation, nationality and age group. Since the onset of AIDS in the early 1980s, the AIDS pandemic has particularly affected the gay community, with gay men comprising approximately two-thirds of all AIDS cases in the United States. However, an increasing number of heterosexual women and men have since become infected, especially among minorities. In the Sub-Sahara region women are disproportionately impacted by HIV/AIDS. In the fight against the spread of AIDS, the medical profession, as well as governmental and health organizations, have strongly advocated the use condoms to combat the transmission of HIV.

Condoms are the only devices available now that provide triple protection against HIV, sexually transmitted infections (STIs) and pregnancy. Further, condoms are inexpensive, and have few side effects. However, while familiarity with condoms is high among most population groups and regions, condom usage, access, and availability around the world are currently inadequate.

Condom usage is inadequate due to basic shortcomings of conventional condoms. Conventionally, condoms are of the common thin rolled variety, typically made of a thin, soft, flaccid material such as latex or polyurethane, or some type of animal intestine. The condom is typically made quite thin in order to provide acceptable tactile stimulation to transfer through the material for the active male user. However, because the condom is made as thin as possible to enhance transferred stimulation, it is susceptible to breakage, thereby exposing the user and the user's partner to sexually transmitted diseases or the risk of unplanned pregnancy. Studies have shown that commercial thin membrane latex male condoms can have a failure rate up to 18%. As such, thin rolled condoms have had an extensive history of consumer complaints regarding their effectiveness in preventing STIs and pregnancy.

Thin rolled condoms have also had an extensive history of consumer dissatisfaction regarding their diminishment of pleasure. It is well known that the use of thin rolled condoms disrupt intimacy; they can pinch and snag the skin, desensitize the sexual experience and generally interfere with the overall pleasure associated with sex. But most importantly, thin rolled condoms diminish pleasure because they overlook the 'fluid factor'. Heterosexual contact normally occurs in the wet, slippery, warm, environment of the vagina that stimulates the orgasmic response between partners. Thin rolled condoms do not permit direct or wet contact between partners to stimulate the orgasmic response.

Thin condoms conventionally come in male and female varieties.

A male condom is of the type worn on the penis by the active male partner during sexual intercourse. The traditional male condom has an elongated tubular sheath, which is open at one end for insertion of the penis, and closed at the other end to trap ejaculate of seminal fluids. A conventional male condom is donned by unrolling and stretching the sheath onto the erect penis fitting snuggly, end to end. In most varieties, the open end generally has a peripheral bead that functions as a constricted rim to prevent the condom from slipping off during use.

Generally, the male condom is elastically fitted to cling to the penis tip, and during coitus it remains outstretched and taut, which can increase the hazard of the condom being torn or bursting during use. The structural integrity of the thin condom can also be compromised by leakage, slippage and viral penetration. Hence, male condoms are well known to be only partially effective in the prevention of sexually transmitted diseases, such as HIV. The CDC evaluates male condom effectiveness at a failure rate of up to 18%, when used correctly and consistently.

Not only do traditional male condoms have an unacceptably high risk of failure, such condoms also suffer from a number of other shortcomings that can discourage their use entirely, thus diminishing their effectiveness in the fight against the spread of AIDS. One drawback is that the use of a condom can interrupt sexual intimacy because the condom has to be donned onto the erect penis after arousal. Another drawback is that after sexual intercourse is completed, the condom may slip off as the erect penis softens, which may cause unwanted leakage of semen and/or contamination.

Yet another disadvantage of the traditional thin male condom is the loss of sensation experienced by the active male caused by the fact that the condom must be tight-fitting in order to stay in place. The conventional condom does not permit adequate sensitivity for the active male during sexual intercourse because it constricts sensation and ignores the fluid anatomy conditional to sexual intercourse. Also, because the rolled condom is fitted to move along clinging to the penis, it prevents direct fluid communication and tactile friction between the penis of the active partner and the vaginal or rectal wall of the passive partner during sexual intercourse.

Not least, most traditional male condoms are typically constructed in a single, standard size, which does not accommodate penises of different sizes in length and girth. Such construction can be uncomfortable for the male wearer when the standard size will not fit.

In addition to male condoms, there are also female condoms, which are barrier devices made to be worn internally by the female partner. The conventional female condom is typically comprised of a thin, pouch liner with a closed end and a large open end that is generally provided with a stiff outer ring, attached to hold the mouth of the liner open outside of the vagina and another inside, loose ring to position the closed end at the cervix.

One of the many disadvantages of a female (i.e. receptive) condom is that there is a risk that the condom can slip or become dislodged during sexual intercourse. For a female condom to be an effective barrier to pregnancy and/or the transmission of sexual diseases, it is essential that, even during repeated and rigorous coitus, the penis does not penetrate the vagina outside the condom (side entry).

Moreover, like most commercial male condoms, female condoms are commonly formed of latex, polyurethane, or nitrile. Because they are made of thin material, such condoms are flaccid and thus susceptible to irregular bunching during use, resulting in discomfort or generally poor performance.

Moreover, such female condoms perform poorly, since their flaccid membranes do not have sufficient structural rigidity to maintain traction between the condom and the female vaginal cavity, which also could result in a risk of the penis penetrating the vagina outside the condom. Also, female condoms evaluated for efficacy by the CDC have up to a 21% failure rate when used correctly and consistently.

SUMMARY OF THE INVENTION

In view of the foregoing, it is an object of the present invention to provide a condom that is safer in terms of breakage, leakage, slippage, and viral permeability than available commercial condoms.

It is an object of the present invention to provide an improved condom for use in receptive intercourse, as either a male condom or a female condom.

It is an object of the present invention to provide an improved condom that is an operative, movable, condom engineered to move in a specific and consistent manner and direction with internal lubrication to create sensation internally, not by transference through the material.

It is an object of the present invention to provide an improved condom of extended length that does not slip off during intercourse.

It is an object of the present invention to provide an improved condom that can loosely accommodate a penis of variable length and girth dimensions so as to provide proper loose fit with extended length and not to cause loss of sensation.

It is an object of the present invention to provide an improved condom with extended length that can readily accommodate penises of different sizes, from small to extra large.

It is an object of the present invention to provide an improved condom that can enhance direct tactile friction and fluid contact between the penis and the internal condom wall during sexual intercourse.

In accordance with the objects of the present invention, the condom of the present invention is 2-3 times thicker than ordinary thin condoms. Due to its thickenss, the condom has superior strength and durability, thereby reducing the risk of tearing or bursting, thus providing greater protection against the transmission of sexually transmitted diseases as well as protection against unintentional pregnancies.

The condom is not only thicker but also much longer than a standard condom proportionate to penis length. Unlike the standard one-size-fits-all condom, the condom according to the present invention comes in different sizes, being at least approximately 20% longer than a standard condom and can be as long as 12" in length, the preferred size being 20% longer than the user's erect penis. The elongated length of the condom prevents breakage at the tip that commonly occurs in thin condoms. Thin condoms are typically snug fitting with one established generic size that is intended to fit to the tip of the penis, which creates concentrated stress at the tip, the primary site for condom breakage according to clinical studies. Since the condom according to the present invention is to be approximately 20% longer than the user's erect penis, the extended length prevents stress concentration at the tip, thereby eliminating the risk of breakage at the tip.

Based on the prescribed thickness and length, and further in accordance with the objects of the present invention, a condom according to an embodiment of the invention has an extended sheath body with an open end and a closed end, with a plurality of longitudinal flutes on the sheath body. A flute is a fold in the condom that defines a curved ridge extending along the longitudinal length of the sheath body.

Figure 5:
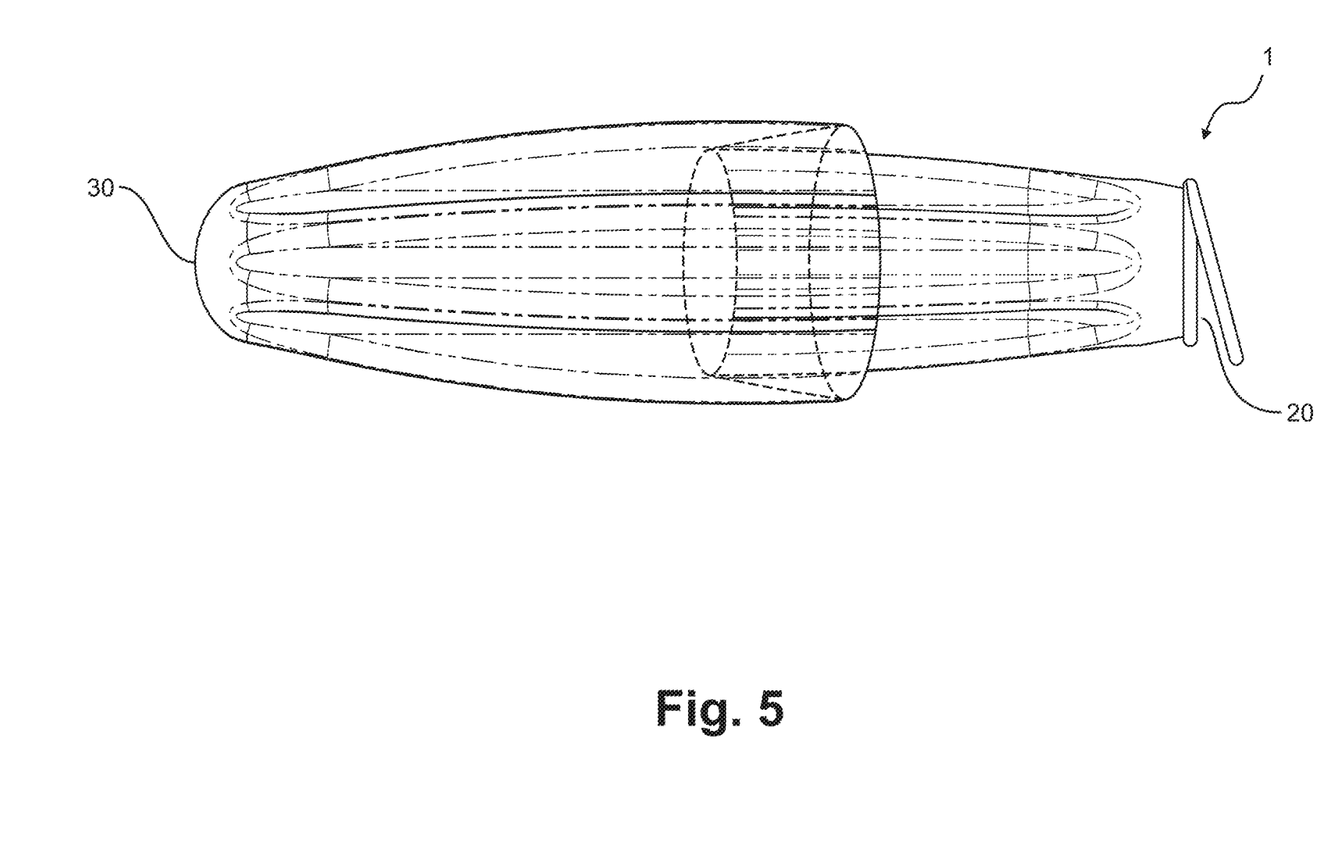
FIG. 5 is a perspective view of a male condom according to an embodiment of the invention in a folded state.

During intercourse, as the penis is thrust forward into the receiving partner, it is pushed into the elongated condom, which causes the condom to billow due to its fluting. As the penis is pushed farther forward into the billowed condom, the condom buckles cross-current to the flutes, folding over on itself due to its extended length as shown in FIG. 5. The condom buckles at its midsection where the elliptical sheath body is widest. The top portion of the condom near the closed end folds back towards the base of the condom near the open end as the penis is pushed towards the extended tip of the closed end. Conversely, when the penis is pulled on the withdrawal stroke, the condom unfolds. In this way, the elongated length helps prevent the condom from sliding off because the normal 'tug' action created by the withdrawal stroke of the penis is absorbed by the extra length of the condom, and this motion is repeated consistently with each thrust and withdrawal movement.

The flutes allow the condom to fold over on itself and unfold to provide a consistent slide-over effect that creates a reciprocating motion during coitus. Unlike a conventional male condom that is designed to be tight-fitting, the fluting allows the penis to move inside the condom as the condom folds and unfolds with consistent regularity. As the extended length of the condom glides back and forth over the penis during intercourse, the movement of the condom, facilitated by the convolutions of the fluted shape of the condom, functions to create and enhance sensation to the penis.

Further, the condom can function with internal lubrication to facilitate consistent fluid movement of the condom gliding over the penis. Since the penis glides inside the condom, direct fluid sensation is created from inside rather than from outside as with typical thin rolled condoms. Thus, unlike conventional thin condoms that are designed as thin as possible to facilitate 'transferred sensation' filtered through the barrier material, the condom of the present invention mechanically creates sensation internally rather than transfer it through the material.

The male condom of the present invention is a non-rolled condom. In an embodiment of the male condom, the condom has two conjoined rings at the open end. A first ring is formed integrally with the lip of the open end. A second ring, larger in diameter than the first ring, is integrally connected to the first ring at a position or positions along the perimeter, such that the rings are capable of being pulled independently for the purpose of donning the condom. Unlike the familiar rolled condom that must be unrolled down the shaft of the penis, which can be difficult for the user to do efficiently, the present condom can be easily donned without unrolling by being pulled on like a sock. The condom is donned by pulling either the first ring or the second ring or both together to slide the condom onto the penis. The smaller first ring is stretched during the donning process and released when it reaches the base of the penis to form a snug fit at the open end. The second ring can be looped over the user's scrotum to anchor the condom in place to help prevent slippage. The second ring also functions to retain blood flow in the erect penis to help maintain an erection.

In summary, the present condom provides a more comfortable fit for the active partner as it loosely accommodates the penis so that tactile fluid movement of the penis is possible during coitus. The condom also provides increased stimulation for the passive partner because the flutes rub against the vaginal or rectal wall during intercourse.

The present condom can also function as a female condom or receptive condom by inserting it into the vaginal or anal cavity prior to sexual activity. The insertion can be performed manually or with an insertion device. As a receptive condom it may be applied prior to intercourse without requiring the participation or acquiescence of the active partner. Since the receptive condom may be inserted before intercourse, it does not necessarily interrupt or interfere with the sexual intimacy. Additionally the receptive condom may first be donned over the erect penis before penetration of the vagina or rectum.

Figure 6:
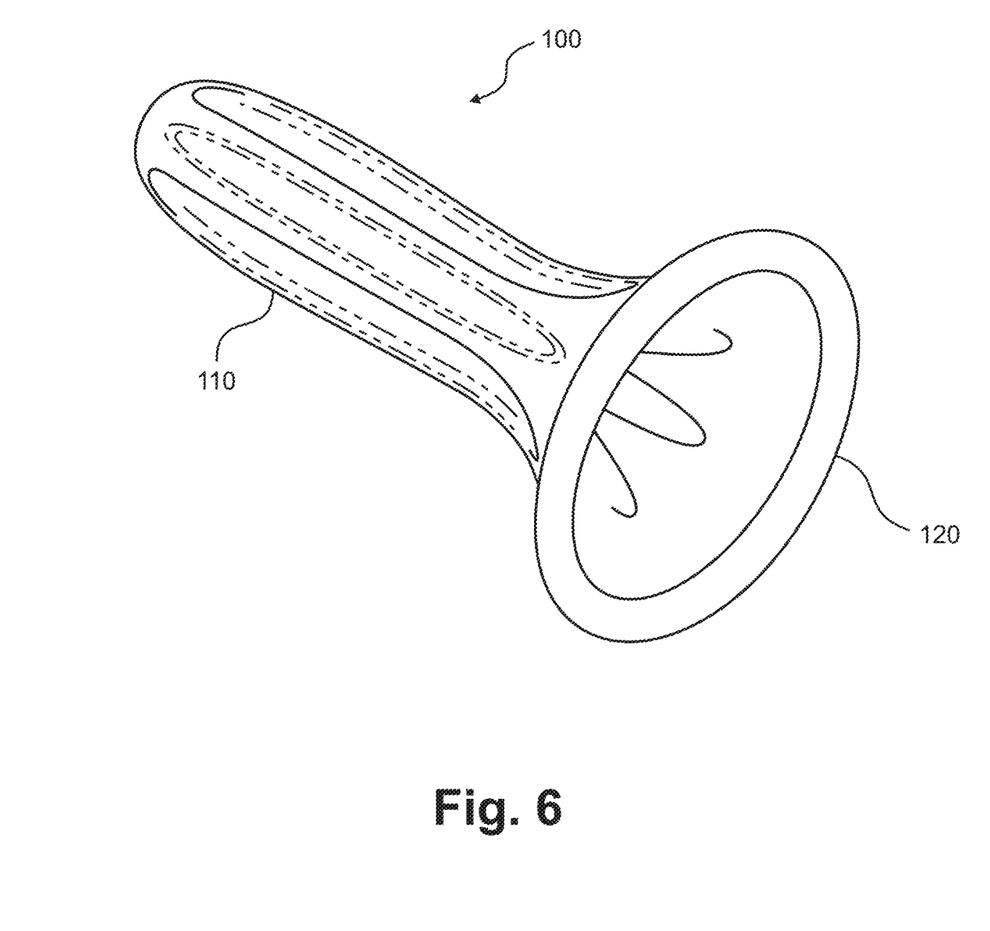
FIG. 6 is a perspective view of a female condom according to an embodiment of the invention.
Figure 7:
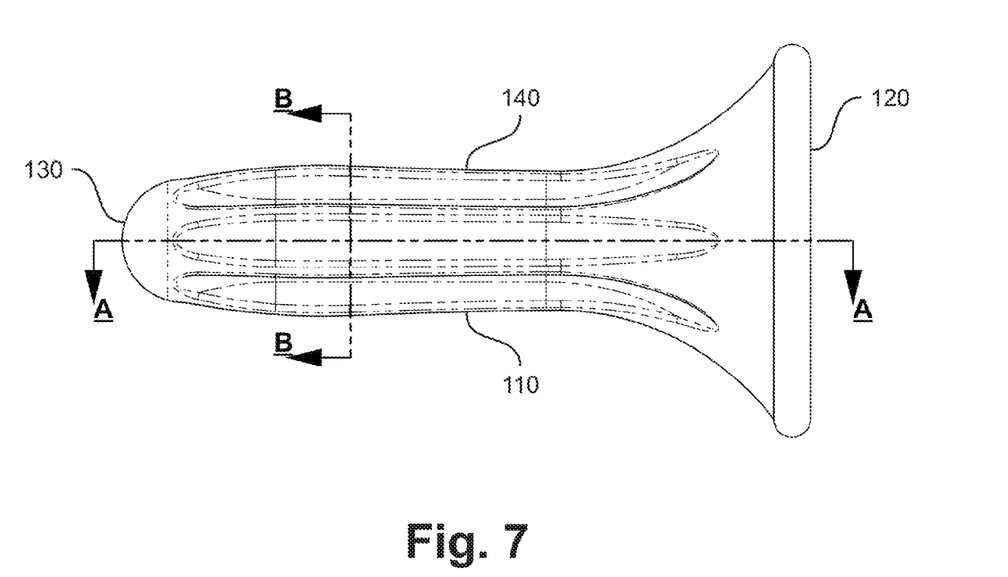
FIG. 7 is a top view of a female condom according to an embodiment of the invention.
Figure 8:
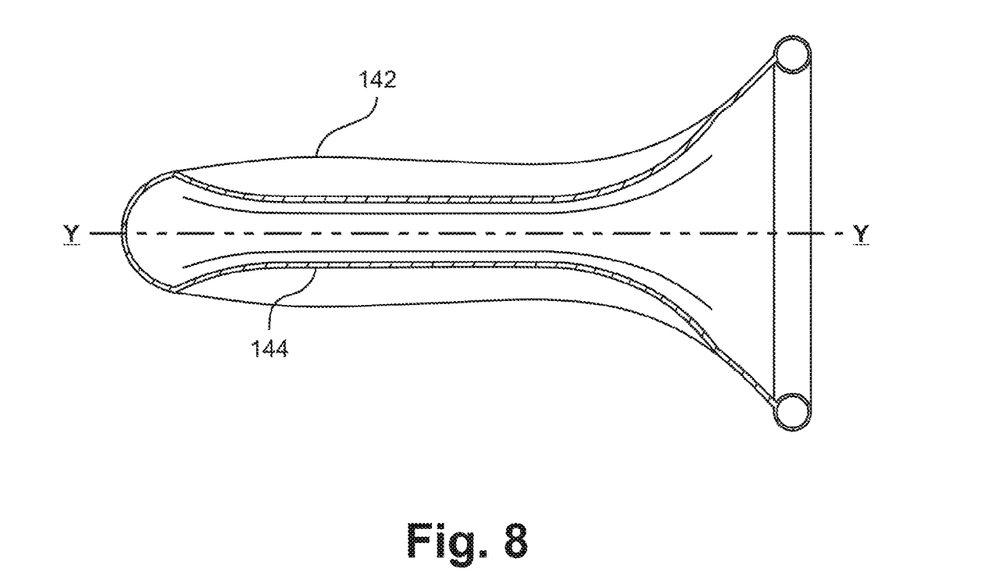
FIG. 8 is a front sectional view of a female condom taken along section A-A of FIG. 7 according to an embodiment of the invention.
Figure 9:
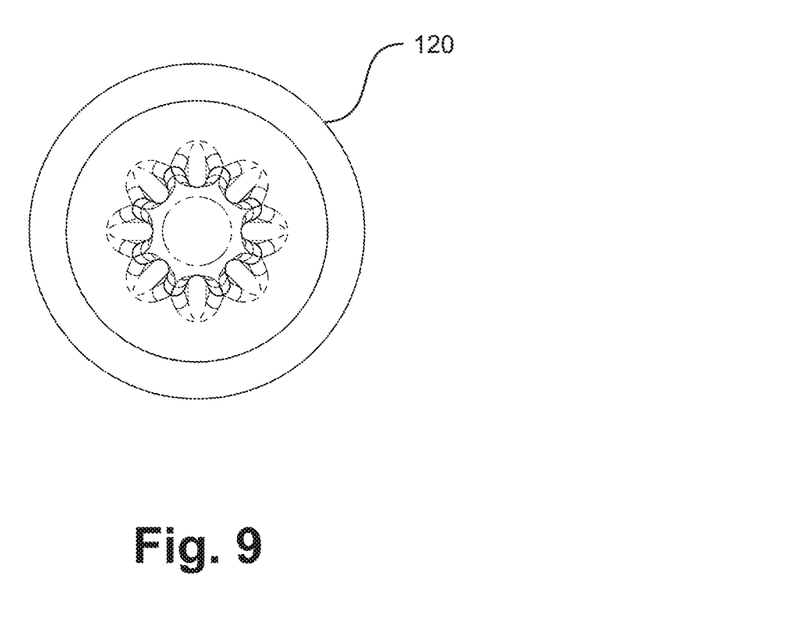
FIG. 9 is a side view of a female condom according to an embodiment of the invention.

FIGS. 6-10 show a female condom according to the present invention, having a sheath body with a proximal end that is open and a distal end that is closed. As shown in FIG. 6, the condom has a plurality of flutes on the sheath body extending between the open end and the closed end. The plurality of flutes form ridges and furrows having a corrugated shape as best shown in FIG. 9. The condom has an enlarged ring at the open end, wherein the ring is tubular and sufficiently sized to remain outside of the vaginal opening to maintain the opening of the condom after insertion. Once inserted the tubular ring is closed or folded in half in a configuration simulating the shape of the labia.

While the foregoing describes the present invention in relation to the drawings and embodiments, it is to be understood that the description is not intended to limit the scope of the invention to the drawings or embodiments described herein. To the contrary, the description is intended to cover all alternative modifications and equivalents that may be included in the spirit and the scope of the invention as defined by the appended claims.

DETAILED DESCRIPTION OF THE INVENTION

A condom according to an embodiment of the invention has a thickness in the range of at least 0.007" (175 micron) to 0.010" (250 micron), which is approximately 2-3 times thicker than thin rolled condoms, which typically range from 0.0025" (60 micron) up to 0.0050" (125 micron). Due to its thickness, the condom of the present invention is shape-retaining, not flaccid like thin rolled condoms. Further, given its distinctive and unique thickness, the condom does not suffer from the common limitations and failures inherent in thin condoms. Most importantly, it is widely known in the art and independent testing has shown that thin condoms do not provide 100% protection against sexually communicable diseases, such as HIV. Under laboratory testing, thin condoms have proven to have deficient strength (e.g. tensile strength and tear resistance properties) and durability, resulting in an average 20% failure rate for viral permeability. Because the condom of the present invention is 2-3 times thicker than ordinary thin condoms, it has superior strength and durability, providing greater protection against the transmission of sexually transmitted diseases as well as protection against unintentional pregnancies. In particular, the thickness of the present condom makes it especially effective protection for anal sex, which is considered a more rigorous activity for which thin rolled condoms are less effective.

In an embodiment of a male condom of the present invention, the condom is not only thicker but also much longer than a standard condom proportionate to penis length. Unlike the standard one-size-fits-all condom, the condom according to the present invention comes in different sizes, being at least approximately 20% longer than a standard condom and can be as long as 12" in length. The user is to select the size of the condom according to the user's anatomical requirements. More particularly, the user is to select the condom having a length that is approximately 20% longer than the user's erect penis.

As shown in FIGS. 1-5, a male condom 1 of the present invention has a sheath body 10 with a proximal end 20 that is open and a distal end 30 that is closed.

Figure 1:
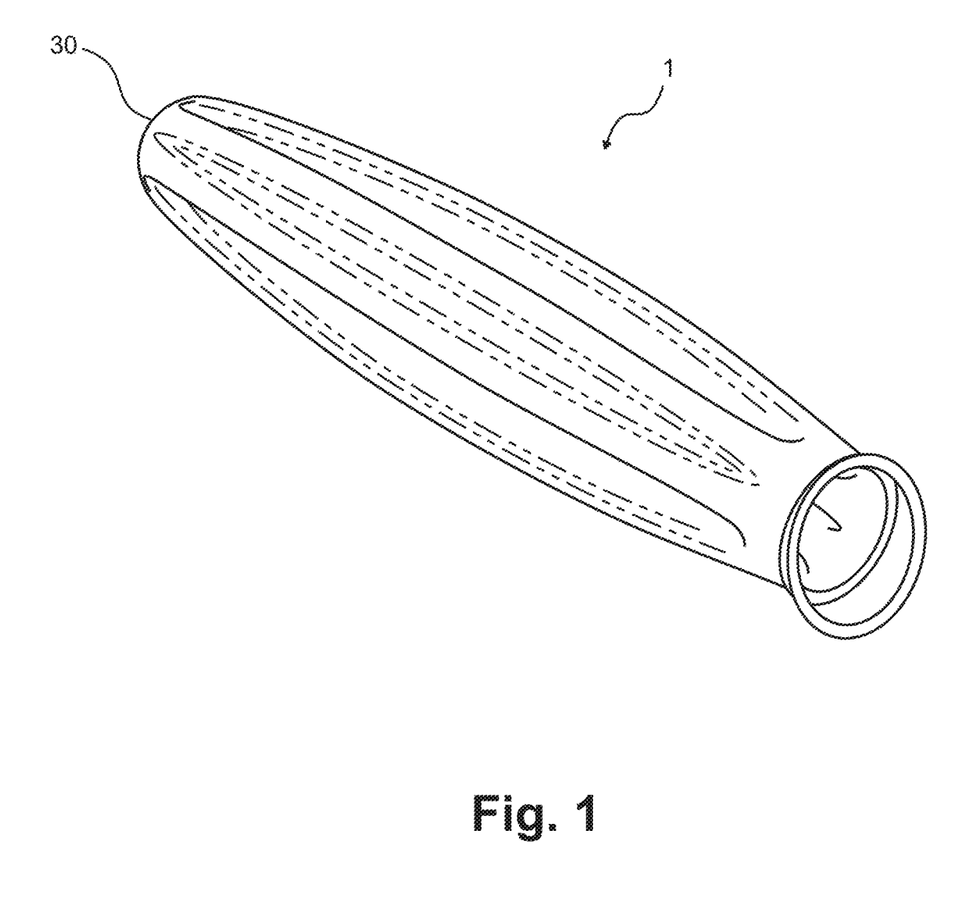
FIG. 1 is a perspective view of a male condom according to an embodiment of the invention.
Figure 2:
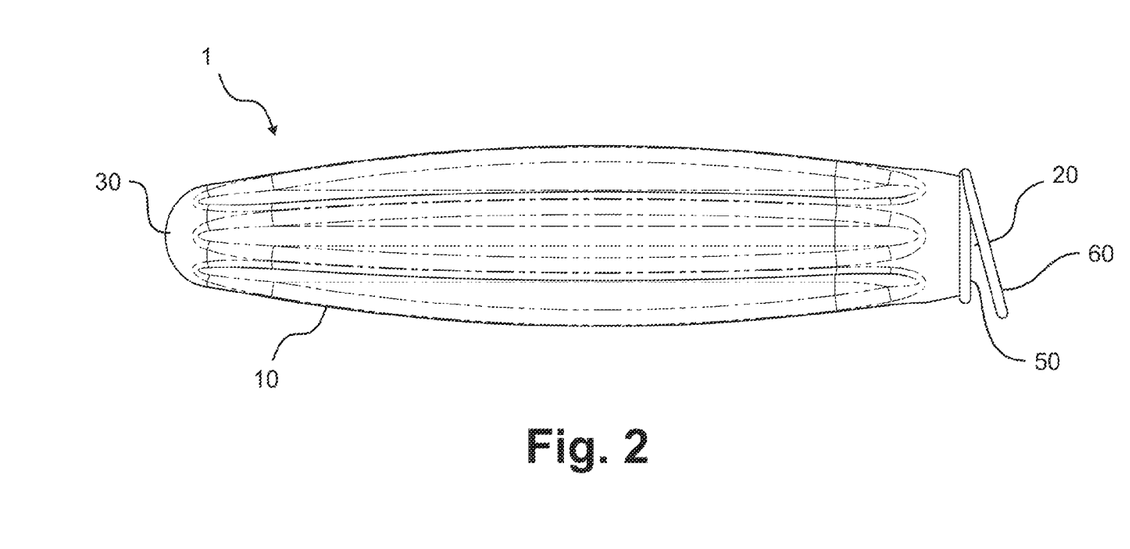
FIG. 2 is a front view of a male condom according to an embodiment of the invention.
Figure 3:
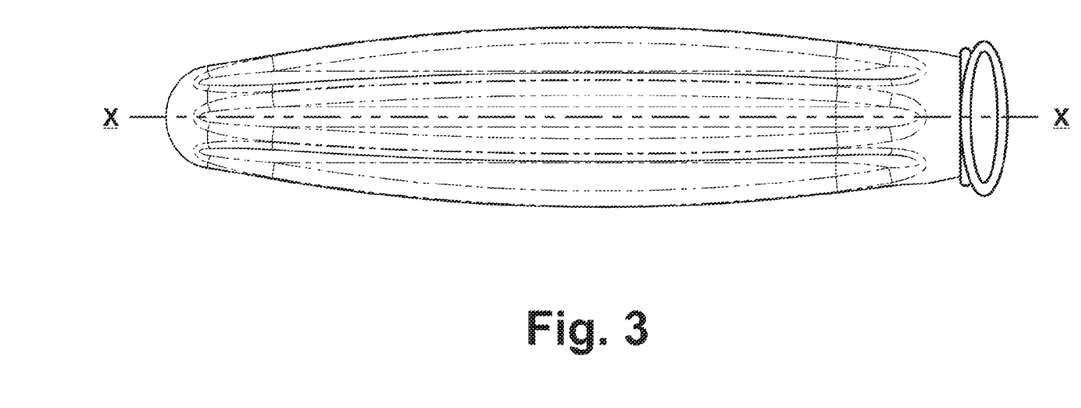
FIG. 3 is a top view of a male condom according to an embodiment of the invention.

In an embodiment of the invention shown in FIG. 2, condom 1 has a plurality of flutes 40 on sheath body 10 extending along a longitudinal axis X-X between open end 20 and closed end 30. Each flute 40 is characterized by a curved ridge 42 extending along longitudinal axis X-X of sheath body 10. The curved ridge 42 is highest at the midsection of body 10 relative to longitudinal axis X-X, and gradually tapers towards the respective ends 20, 30, such that the sheath body 10 has an elliptical shape characterized by a midsection that is wider than the respective ends as shown in FIG. 3. The elliptical shape of the sheath body 10 is in contrast to the straight, tubular shape of a conventional thin condom when it is unrolled.

Figure 4:
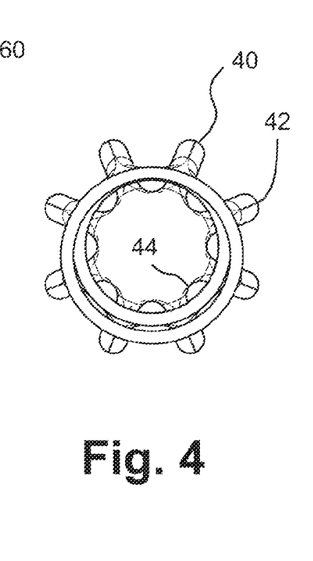
FIG. 4 is a side view of a male condom according to an embodiment of the invention.

As shown in FIG. 4, the plurality of flutes 40 is thus defined by curved ridges 42 and furrows 44 that form a corrugated shape, having a serpentine or undulating profile. A cross-section of the condom 1 would look similar to an asterisk, with the flutes 40 extending radially from the center core of the condom 1 as shown in FIG. 4.

In the embodiment of the male condom shown in FIGS. 1-5, condom 1 has a first ring 50 located at the open end 20. The condom 1 can be donned by pulling first ring 50 so that the sheath body 10 slides onto the penis like a sock. The condom 1 is not like a traditional thin condom that must be unrolled down the shaft of the penis, which can be difficult for the user to do efficiently. Rather, the condom 1 can be easily donned without unrolling by pulling the first ring 50 to slide the condom 1 onto the penis like a sock.

The open end 20 with first ring 50 is sized to fit tightly around the base of the penis to prevent slippage and spillage of semen. Because the open end 20 fits snuggly around the base of the penis, the condom 1 will billow or swell when the penis is inserted into the condom 1 because some air is trapped in the condom 1 due to its extended length. The flutes 40 function as air channels to evacuate the air when the condom 1 is donned to prevent the formation of an air pocket.

In another embodiment, condom 1 also has a second ring 60 that is integrally connected to the first ring 50 as shown in FIGS. 2-3. The second ring 60 can also be pulled to don the condom 1 like a sock. The second ring 60 can be looped over a user's scrotum to anchor the condom to prevent slippage.

For this purpose, the second ring 60 is typically larger in diameter than the first ring 50.

During intercourse, as the penis is thrust forward into the receiving partner, it is pushed into the elongated condom 1, which causes the condom 1 to billow. As the penis is pushed farther forward into the billowed condom, the condom 1 buckles cross-current to the flutes, folding over on itself due to its extended length as shown in FIG. 5. The condom 1 buckles at its midsection where the elliptical sheath body is widest. The top portion of the condom 1 near the closed end 30 folds back towards the base of the condom near the open end 20 as the penis is pushed towards the extended tip of the closed end 30. Conversely, when the penis is pulled on the withdrawal stroke, the condom 1 unfolds. In this way, the elongated length helps prevent the condom 1 from sliding off because the normal 'tug' action created by the withdrawal stroke of the penis is absorbed by the extra length of the condom 1, and this motion is repeated consistently with each thrust and withdrawal movement.

The flutes 40 allow the condom 1 to fold over on itself and unfold without becoming tangled or bunched, providing a consistent slide-over effect that creates a reciprocating motion that is in fluid concert with bodily motion. Unlike a conventional male condom that is designed to be tight-fitting in order to cling to the penis and to move along with the penis, thereby restricting sensation, the fluting 40 allows the penis to move inside the sheath body 10 as the condom 1 folds and unfolds with consistent regularity. As the extended length of the condom 1 glides back and forth over the penis during intercourse, the movement of the condom, facilitated by the convolutions of the fluted shape, functions to create and enhance sensation to the penis.

Further, the condom 1 can function with internal lubrication to facilitate consistent fluid movement of the sheath body 10 gliding over the penis. The fluid movement of the sheath body 10 gliding over the penis simulates the feeling of wet, slippery sexual contact that normally occurs in the wet, slippery, warm, environment of the vagina to stimulate orgasmic response. Since the penis glides inside the condom 1, direct fluid sensation is created from inside rather than from outside as with typical thin rolled condoms. Thus, unlike conventional thin condoms that are designed as thin as possible to facilitate 'transferred sensation' filtered through the barrier material, the condom 1 of the present invention mechanically creates sensation internally rather than transfer it through the material. Further, since the lubricant is viscous, the inner walls cling to the penis and reduce the amount of air that could otherwise be trapped prior to donning. Trapped air could cause the condom 1 to have an undesirable air pocket that would cause the condom 1 to balloon up after donning.

Not only does the condom 1 improve sensation, it is also safer than typical thin condoms. Because the condom 1 is thicker than thin condoms, the condom 1 has greater tensile strength, thereby reducing the risk of the condom tearing or bursting.

In particular, the elongated length of the condom 1 prevents breakage at the tip that commonly occurs in thin condoms. Thin condoms are typically snug fitting with one established generic size that is intended to fit to the tip of the penis, which creates concentrated stress at the tip, the primary site for condom breakage according to clinical studies. The condom 1 reduces the risk of breakage at the tip because the condom designed to be longer than the erect penis on which it is donned. Because condom 1 is to be approximately 20% longer than the user's erect penis, this prevents stress concentration at the tip, thereby eliminating the risk of breakage at the tip. Additionally, the condom 1 can be manufactured by double-dipping the tip for reinforcement to further prevent the most common incidents of breakage at the tip.

In summary, the condom 1 provides a more comfortable fit for the active partner as it loosely accommodates the penis so that tactile fluid movement of the penis is possible during coitus. The condom 1 also provides increased stimulation for the passive partner because the flutes rub against the vaginal or rectal wall during intercourse.

Figure 10:
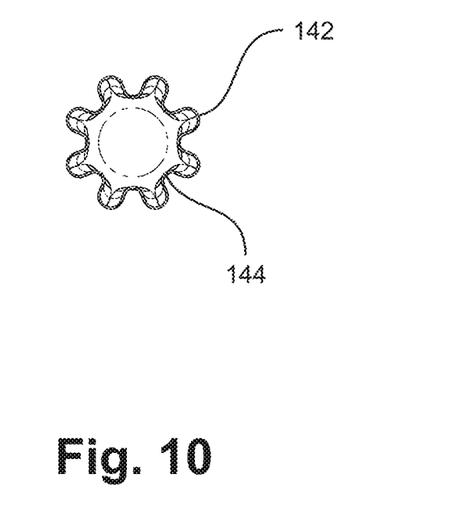
FIG. 10 is a side sectional view of a female condom taken along section B-B of FIG. 7 according to an embodiment of the invention.

FIGS. 6-10 shows a female condom 100 according to an embodiment of the present invention. As shown in FIGS. 6-10, the female condom 100 has a sheath body 110 with a proximal end 120 that is open and a distal end 130 that is closed. The condom 100 has a plurality of flutes 140 on sheath body 110 extending along a longitudinal axis Y-Y between open end 120 and closed end 130. Each flute 140 is characterized by a curved ridge 142 extending along longitudinal axis Y-Y of sheath body 10. The ridge 142 gradually tapers towards the respective ends 20, 30 as best shown in FIG. 8. The plurality of flutes 140 form curved ridges 142 and furrows 144 having a corrugated shape as best shown in FIG. 10. The condom 100 has an enlarged tubular ring 150 at open end 120, wherein the tubular ring 150 is sufficiently sized to remain outside of the vaginal opening to maintain the opening of the condom 100 after insertion.

I claim:

1. A condom comprising:
   a body with an open end and a closed end, said body extending along a longitudinal axis;
   a plurality of flutes on said body between said open end and said closed end;
   each said flute characterized by a fold in the condom that defines a curved ridge extending along said longitudinal axis of said body that is centered with respect to said open and closed ends;
   said curved ridge being highest at the midsection of said body relative to said longitudinal axis, and gradually tapers towards said respective ends;
   said plurality of flutes forming curved ridges and furrows having a corrugated shape;
   wherein said flutes allow said condom to fold and unfold without becoming bunched during sexual intercourse, providing a consistent slide-over effect that creates a reciprocating motion that is in concert with bodily motion.

2. The condom of claim 1 further comprising:
   a first ring located at said open end;
   wherein said first ring can be pulled to put on said condom without unrolling said condom.

3. The condom of claim 2 further comprising a second ring integrally connected to said first ring;
   wherein said second ring can be looped over a user's scrotum to anchor said condom to prevent slippage.

4. The condom of claim 3, wherein said second ring is larger in diameter than said first ring, and said second ring is integrally connected to said first ring at a single position.

5. The condom of claim 1, wherein said condom is up to 12 inches long in an unstretched state.

6. A condom comprising:
   a body with an open end and a closed end, said body extending along a longitudinal axis;
   a plurality of flutes on said body between said open end and said closed end;
   each said flute characterized by a fold in the condom that defines a curved ridge extending along said longitudinal axis of said body that is centered with respect to said open and closed ends;

said curved ridge being highest at the midsection of said body relative to said longitudinal axis, and gradually to ers towards said respective ends;

said plurality of flutes forming curved ridges and furrows having a corrugated shape;

a first ring located at said open end;

a second ring integrally connected to said first ring.

7. A female condom comprising:

a body with an open end and a closed end, said body extending along a longitudinal axis;

a plurality of flutes on said body between said open end and said closed end;

each said flute characterized by a fold in the condom that defines a curved ridge extending along said longitudinal axis of said body that is centered with respect to said open and closed ends;

said curved ridge being highest at the midsection of said body relative to said longitudinal axis, and gradually to ers towards said respective ends;

said plurality of flutes forming curved ridges and furrows having a corrugated shape;

a ring at said open end;

wherein said ring remains outside of vaginal opening to maintain an opening of said condom after insertion.

8. The female condom of claim 7, wherein said ring is tubular.

* * * * *